United States Patent [19]

Monteleone et al.

[11] Patent Number: 5,545,763

[45] Date of Patent: Aug. 13, 1996

[54] 1-OXO-SUBSTITUTED AND UNSUBSTITUTED ISOBUTYL-4-ETHOXY-BENZENES AND MIXTURES THEREOF WITH BICYCLOPENTADIENE DERIVATIVES, USES OF SAME IN PERFUMERY AND METHODS FOR PREPARING SAME

[75] Inventors: Michael G. Monteleone, Hazlet; Richard A. Weiss, Pine Brook; Mark D. Evans, Plainsboro; Marie R. Hanna, Keyport, all of N.J.

[73] Assignee: International Flavors & Fragrances Inc., New York, N.Y.

[21] Appl. No.: 428,420

[22] Filed: Apr. 25, 1995

Related U.S. Application Data

[62] Division of Ser. No. 299,966, Sep. 2, 1994, Pat. No. 5,462,923.

[51] Int. Cl.$^6$ .................................................. C07C 41/18
[52] U.S. Cl. .......................... 568/630; 568/319; 568/322; 568/648
[58] Field of Search .................................. 568/320, 322, 568/814, 319, 372, 648, 630

[56] References Cited

U.S. PATENT DOCUMENTS

| | | | |
|---|---|---|---|
| 4,960,943 | 10/1990 | Botta et al. | 568/322 |
| 4,996,374 | 2/1991 | Lin et al. | 568/814 |
| 5,064,844 | 4/1991 | Van Leeuwen et al. | 568/814 |

OTHER PUBLICATIONS

Dulton et al, Canadian Journal of Chemistry, vol. 31, pp. 138–140 (1953).

Olah, Friedel–Crafts & Related Reactions vol. III, p. 186 (1964).

*Primary Examiner*—James H. Reamer
*Attorney, Agent, or Firm*—Arthur L. Liberman

[57] ABSTRACT

Described are 1-oxo-substituted and unsubstituted isobutyl-4-ethoxy-benzenes and mixtures thereof with bicyclopentadiene derivatives, wherein the 1-oxo-substituted and unsubstituted isobutyl-4-ethoxy-benzenes are defined according to the structure:

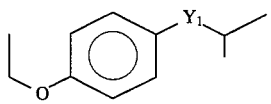

wherein $Y_1$ represents one of the moieties:

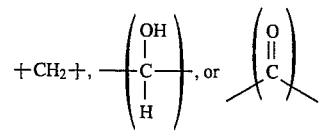

and wherein the bicyclopentadiene derivatives are defined according to the structure:

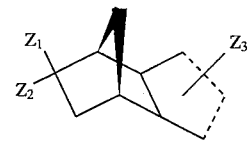

wherein $Z_1$ and $Z_2$ represent hydrogen, $C_1$–$C_3$ lower alkyl or $C_2$–$C_3$ acyl and $Z_3$ represents methyl or hydrogen with the proviso that $Z_1$ and $Z_2$ are not both hydrogen, and uses thereof in augmenting, enhancing or imparting aromas in and to perfume compositions, colognes, perfumed polymers and perfumed articles. Also described is a process for preparing one or both of the compounds having the structures:

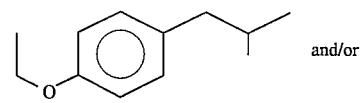

and/or

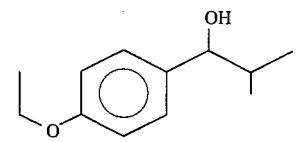

by means of first preparing the compound having the structure:

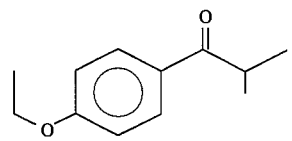

by reacting the compound having the structure:

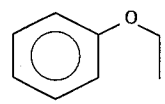

with the compound having the structure:

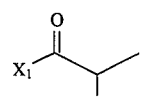

where $X_1$ represents chloro, bromo or hydroxyl and then reacting the compound having the structure:

(Abstract continued on next page.)

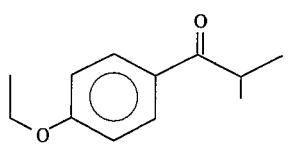
with hydrogen in the presence of an appropriate catalyst under appropriate reaction conditions.
3 Claims, 6 Drawing Sheets

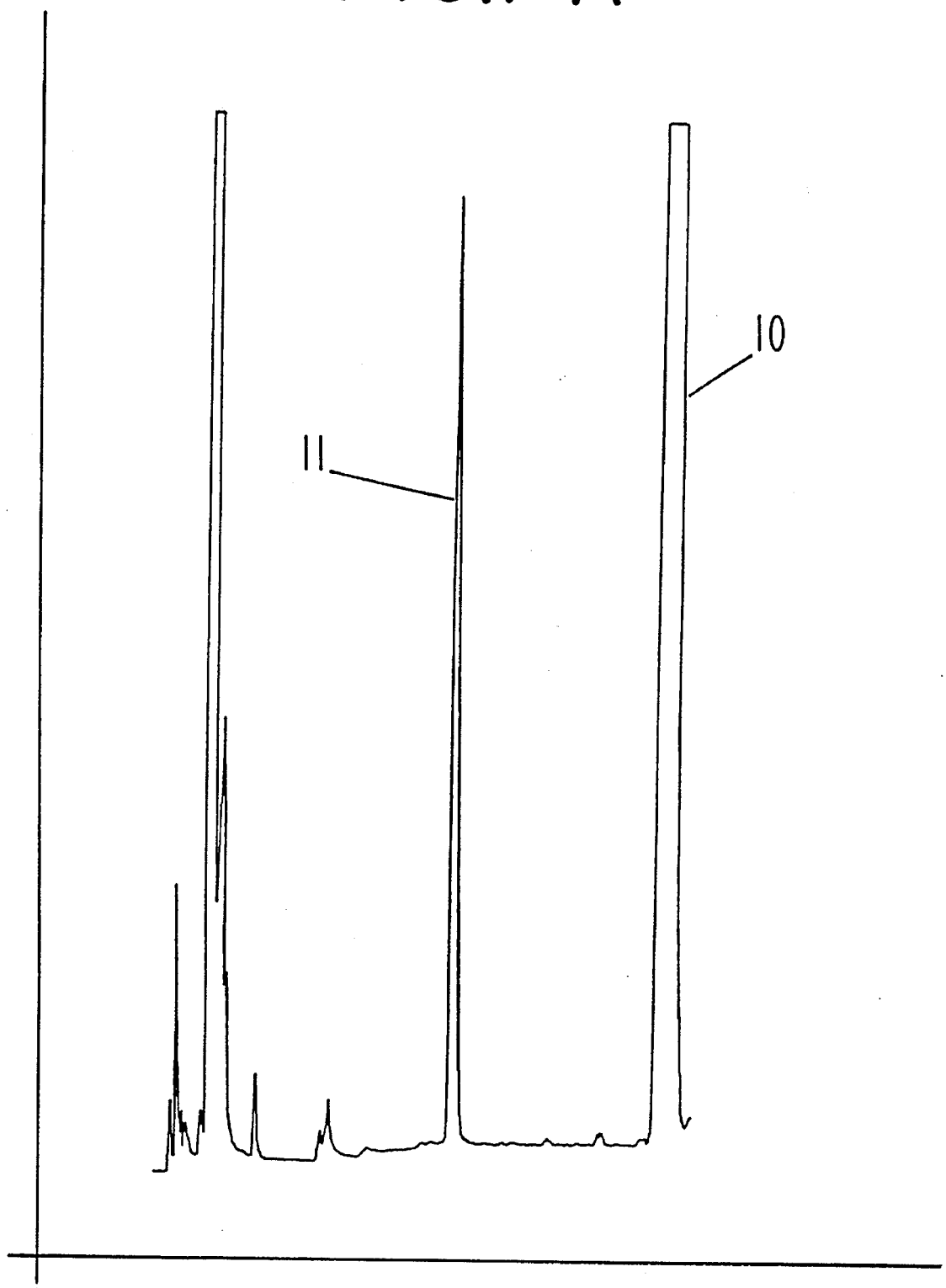
FIG.1-A
GLC PROFILE FOR EXAMPLE I.
CRUDE

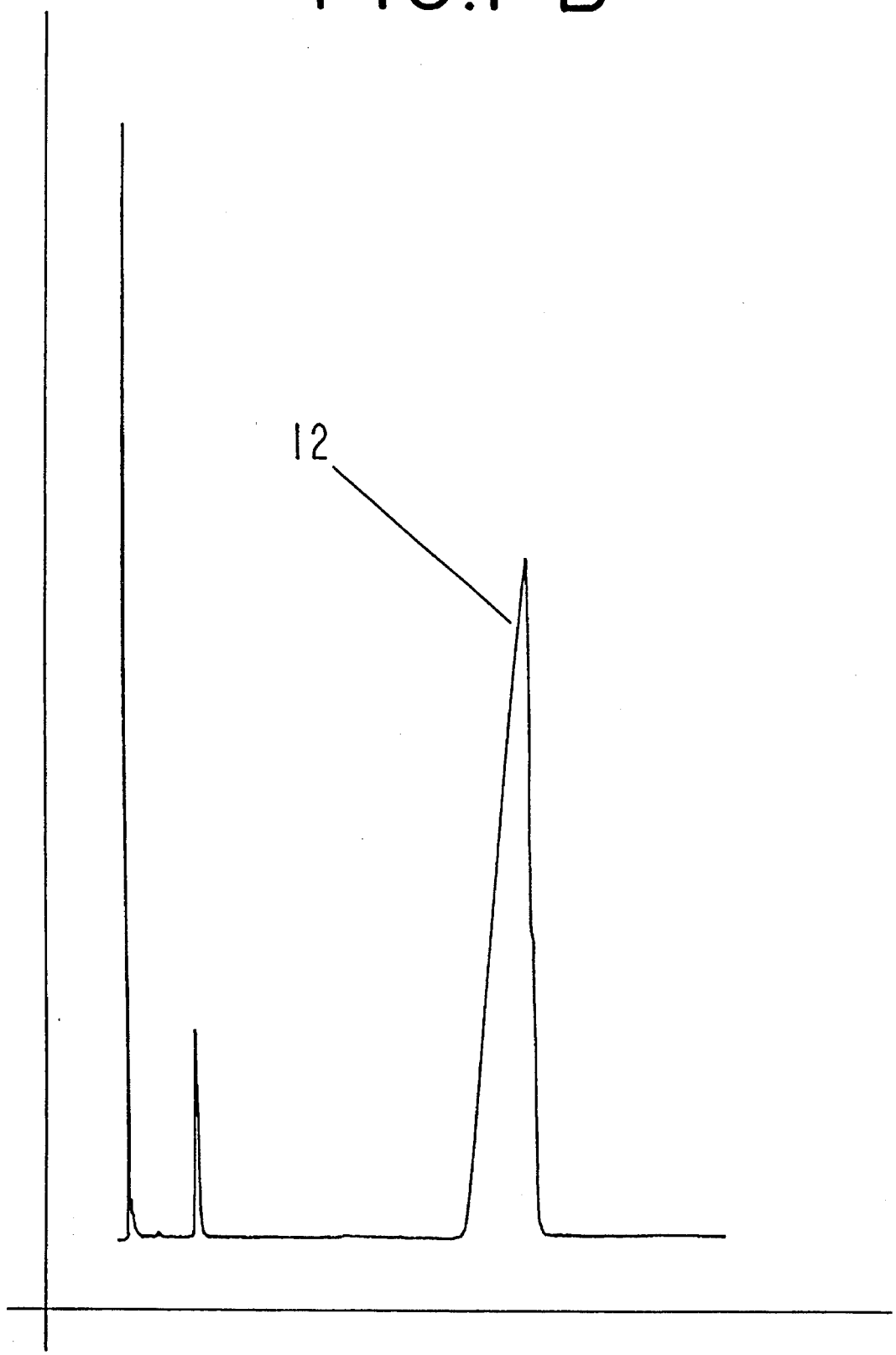
FIG.1-B
GLC PROFILE FOR EXAMPLE I.

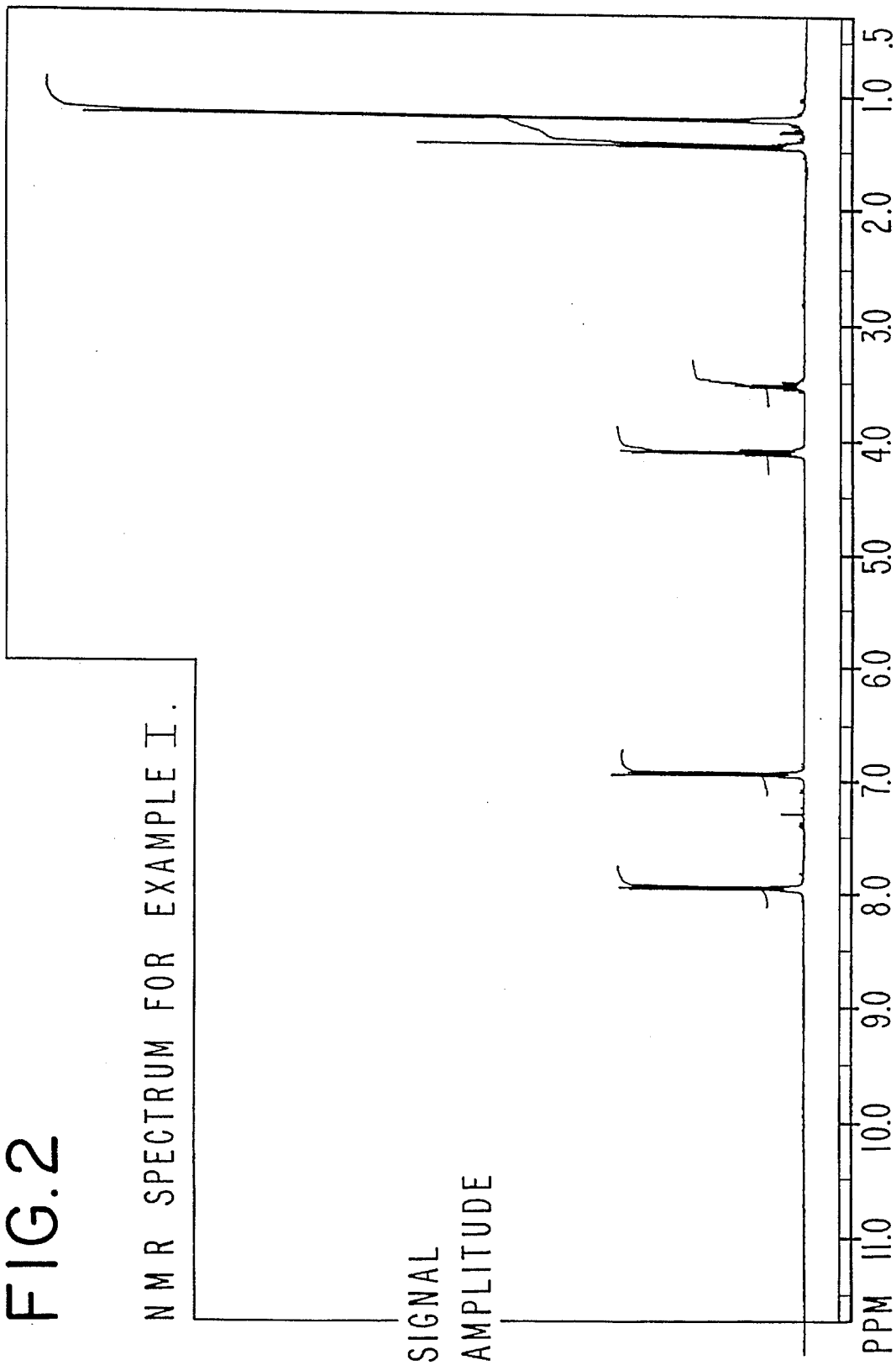

GLC PROFILE FOR EXAMPLE II.

1-OXO-SUBSTITUTED AND UNSUBSTITUTED ISOBUTYL-4-ETHOXY-BENZENES AND MIXTURES THEREOF WITH BICYCLOPENTADIENE DERIVATIVES, USES OF SAME IN PERFUMERY AND METHODS FOR PREPARING SAME

This is a Divisional of application Ser. No. 08/299,966 filed on Sep. 2, 1994 now U.S. Pat. No. 5,462,923 issued on Oct. 31, 1995.

BACKGROUND OF THE INVENTION

Our invention relates to 1-oxo-substituted and unsubstituted isobutyl-4-ethoxy-benzenes and mixtures thereof with bicyclopentadiene derivatives wherein the 1-oxo-substituted and unsubstituted isobutyl-4-ethoxy-benzenes are defined according to the structure:

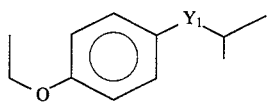

wherein $Y_1$ represents one of the moieties:

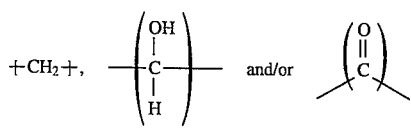

and wherein one of the bicyclopentadiene derivatives is represented by the structure:

wherein $Z_1$ and $Z_2$ are the same or different $C_1$–$C_3$ lower alkyl, $C_2$–$C_3$ acyl or hydrogen and $Z_3$ represents methyl or hydrogen with the provisio that $Z_1$ and $Z_2$ are not both hydrogen.

There has been considerable work performed relating to substances which can be used to impart (modify, augment or enhance) fragrances to (or in) various consumable materials. These substances are used to diminish the use of natural materials, some of which may be in short supply and to provide more uniform properties in the finished product.

Long-lasting, intense, substantive green, woody, privet hedge-like (*Ligustrum vulgare*)-like, floral, lilac, ozoney, phenyl and anisic aromas with fruity, fresh green, ozoney, fresh air, "ocean breeze", and anisic topnotes are highly desirable in several types of perfume compositions, perfumed articles and colognes (e.g., fruity and floral fragrances).

Perfume uses of ethoxy benzene derivatives are well known in the literature. Thus, Arctander "Perfume and Flavor Chemicals (Aroma Chemicals)", Volume I, published in 1969 by the author at Monograph No. 713 discloses the compound having the structure:

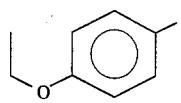

for use in perfumery. Arctander discloses that the compound having the structure:

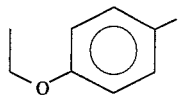

has a powerful, pungent-floral, deep-sweet, warm odor suggestive of Ylang-Ylang, Pandanus and other exotic flowers. Arctander indicates that this compound is useful in perfume compositions of the heavy-floral type, in artificial Ylang-Ylang, and in various types of soap perfumes and in general as a floralizer with considerable power. Arctander further states that the compound having the structure:

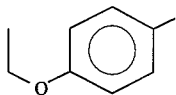

has a "peculiar nut-like, or earthy undertone". Bielstein E, II, 6, 488, H6, System 530a, 522–523 (abstract of Le Brazidec, Bull.Soc.Chim.France[4], 31 263) discloses that the compound having the structure:

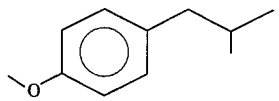

has an anisic aroma. The synthesis of this compound is disclosed by Le Brazidec and is further disclosed by Dutton, et al, Canadian Journal of Chemistry, 31 (1953), 1138, 1140. The structure:

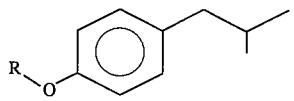

wherein R is methyl is shown by Bielstein, Volume E, IV6, at page 3288 and is also disclosed at Chem. Abstracts, Volume 47, No. 2716h (abstract of J.Elisha Mitchell Sci-.Soc., Volume 66, 171–4 (1950). The compound having the structure:

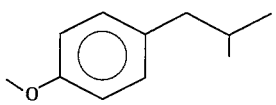

is also disclosed in Schoot, et al, U.S. Pat. No. 2,996,514.
The compounds having the structures:

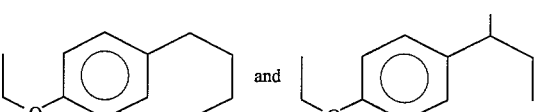

are indicated to be prepared by Chem. Abstracts, Volume 73, 1970, 66192c. The preparation of the compound:

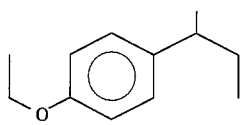

is also shown to be prepared by Bielstein, E IV 6, at page 3280, Chem. Abstracts, 1961, 13386d (Zavgorodnii II) and Chem.Abstracts Volume 49, (1955) No. 8848z (Zavgorodnii I).

Furthermore, the compound having the structure:

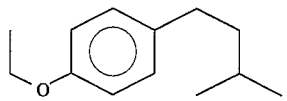

is shown to be prepared by Zavgorodnii III at Chem.Abstracts Volume 71 (1969) No. 3088m. The compound having the structure:

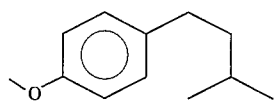

is shown to be prepared using the compound having the structure:

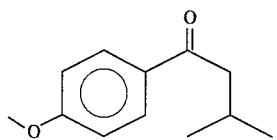

as a starting material according to the reaction:

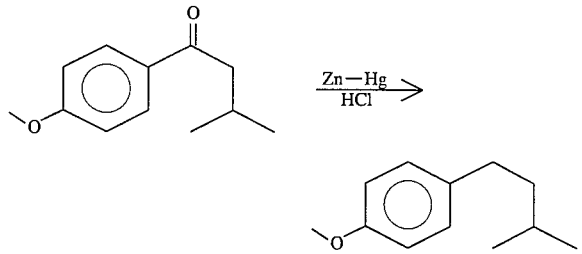

by Bielstein E III 6, H6, 548. The compound having the structure:

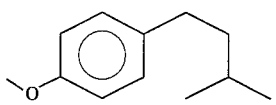

is shown to be prepared using as a starting material the compound having the structure:

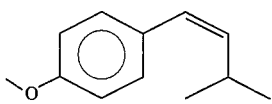

according to the reaction:

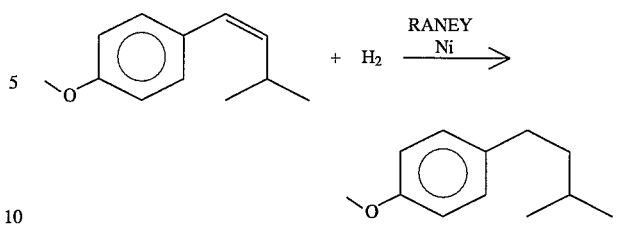

by Bielstein E IV 6, page 3378 and by Dutton, et al, Canadian Journal of Chemistry 31 (1953) pages 1138, 1142.

The compound having the structure:

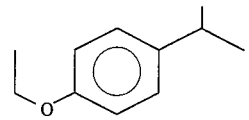

is shown to be prepared by Bielstein E III 6, H6, 505–6 System No. 530, abstract of Ipatieff, et al, Journal of American Soc. 60 (1938) 1161 and Bert, Bull.Soc.Chim. 37, 1252–70 (1925).

For use in perfumery, compounds having the structures:

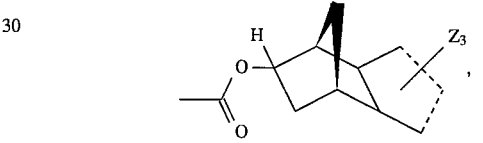

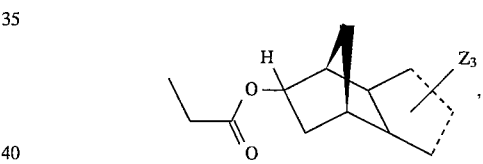

and

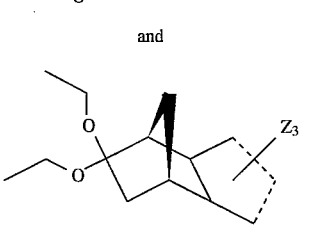

where $Z_3$ is hydrogen is disclosed in the International Flavors & Fragrances Inc. "Fragrance Ingredient Specification Compendium" published by International Flavors & Fragrances Inc. at pages 19, 20 and 72 and in the International Flavors & Fragrances Inc. "Perfumers Compendium" at pages 9 and 36.

Nothing in the prior art, however, discloses the unexpected, unobvious and advantageous organoleptic properties of the 1-oxo-substituted and unsubstituted isobutyl-4-ethoxybenzenes and mixtures thereof with bicyclopentadiene derivatives of our invention.

BRIEF DESCRIPTION OF THE DRAWINGS

FIG. 1A is a GLC profile of the reaction product (crude) of Example I containing the compound having the structure:

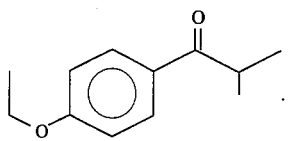

FIG. 1B is the GLC profile for the distilled product of Example I containing the compound having the structure:

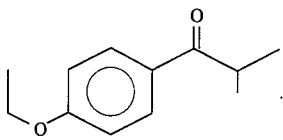

FIG. 2 is the NMR spectrum for the compound having the structure:

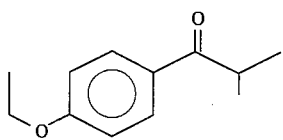

prepared according to Example I.

Figure 3:
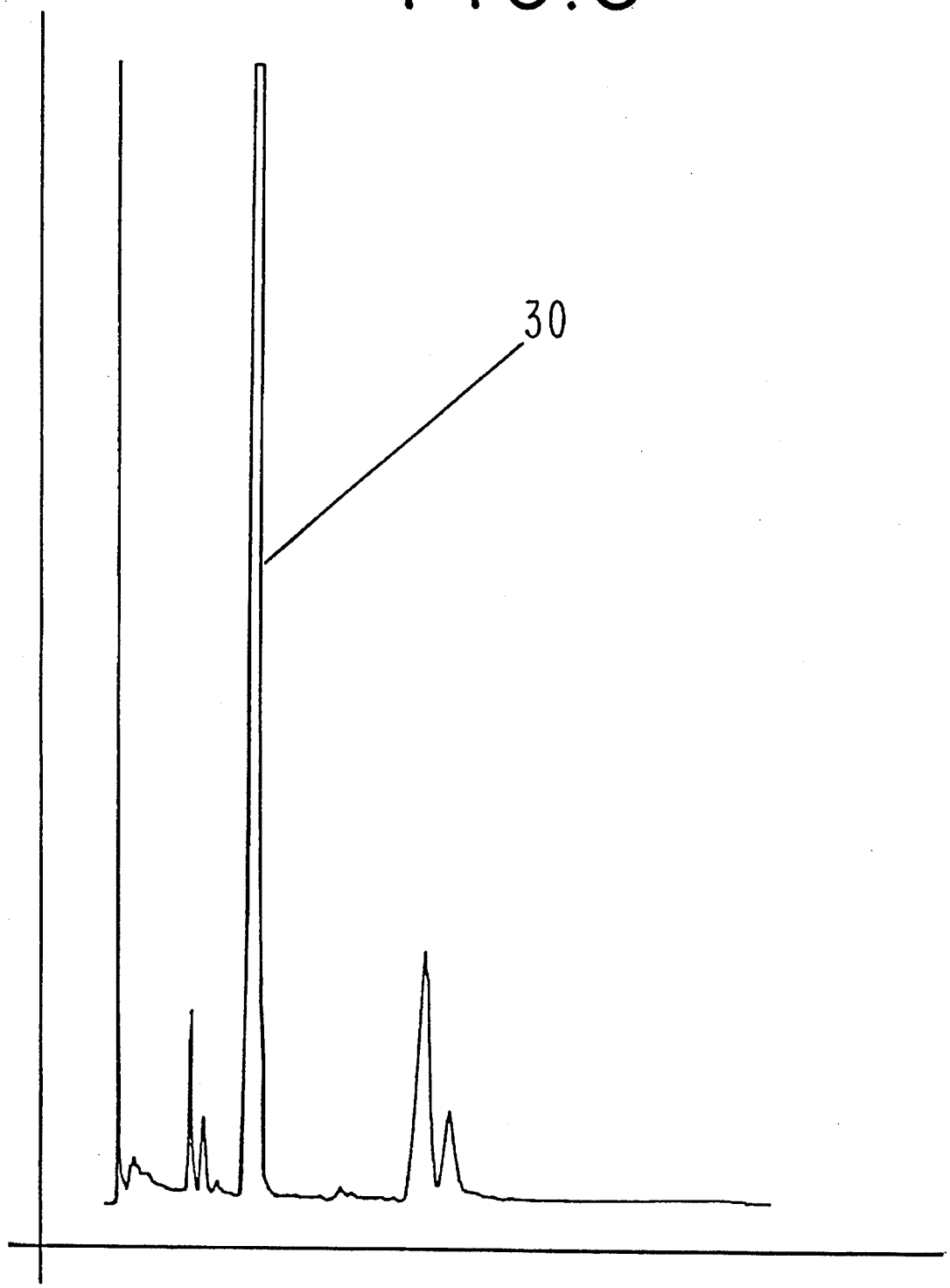

FIG. 3 is the GLC profile for the crude reaction product of Example II containing the compounds having the structures:

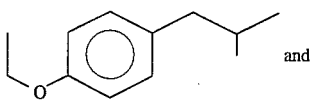

and

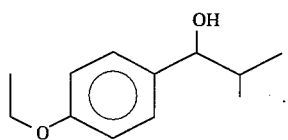

Figure 4:
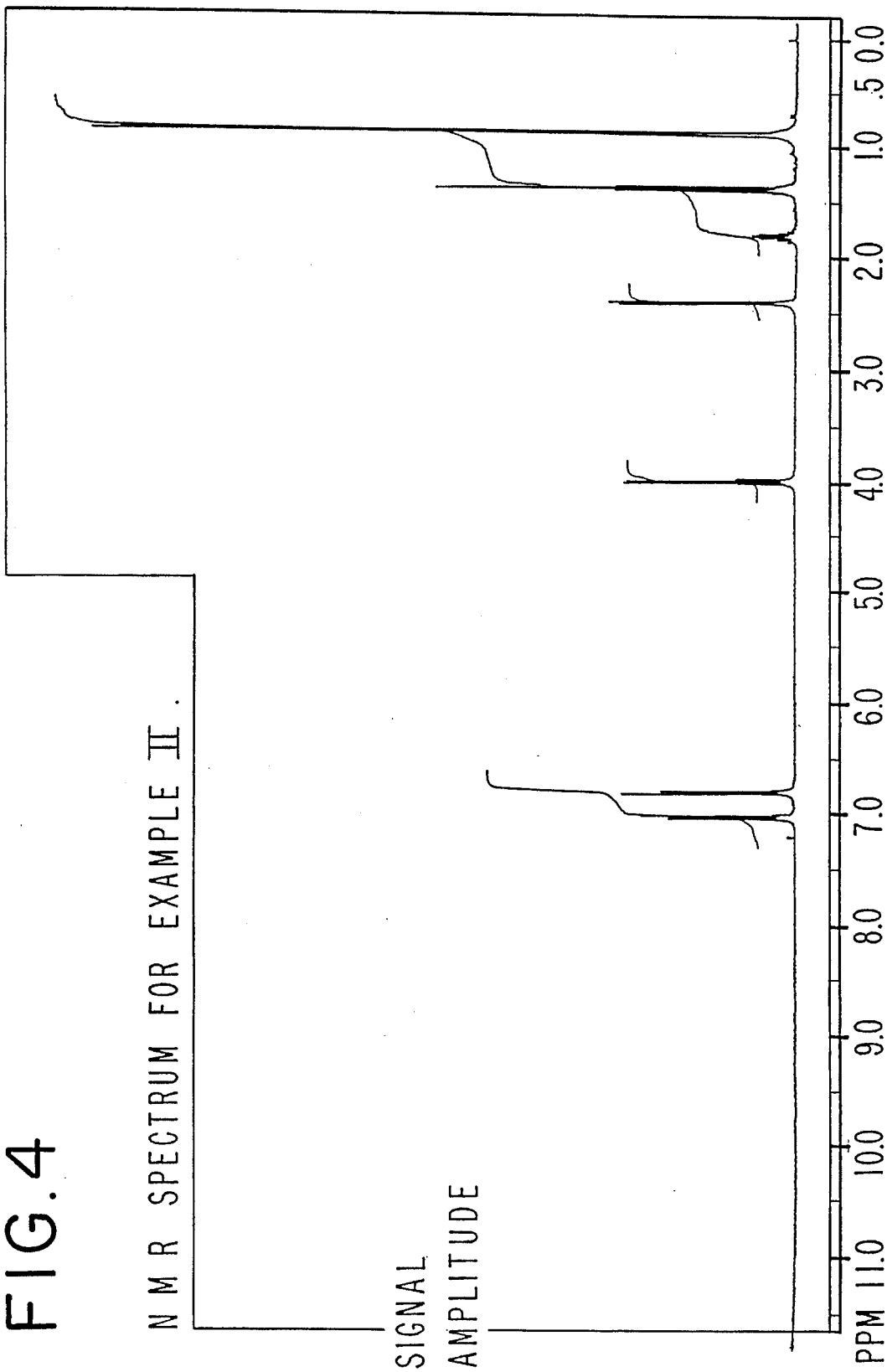

FIG. 4 is the NMR spectrum for the compound having the structure

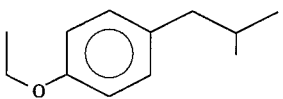

prepared according to Example II.

Figure 5:
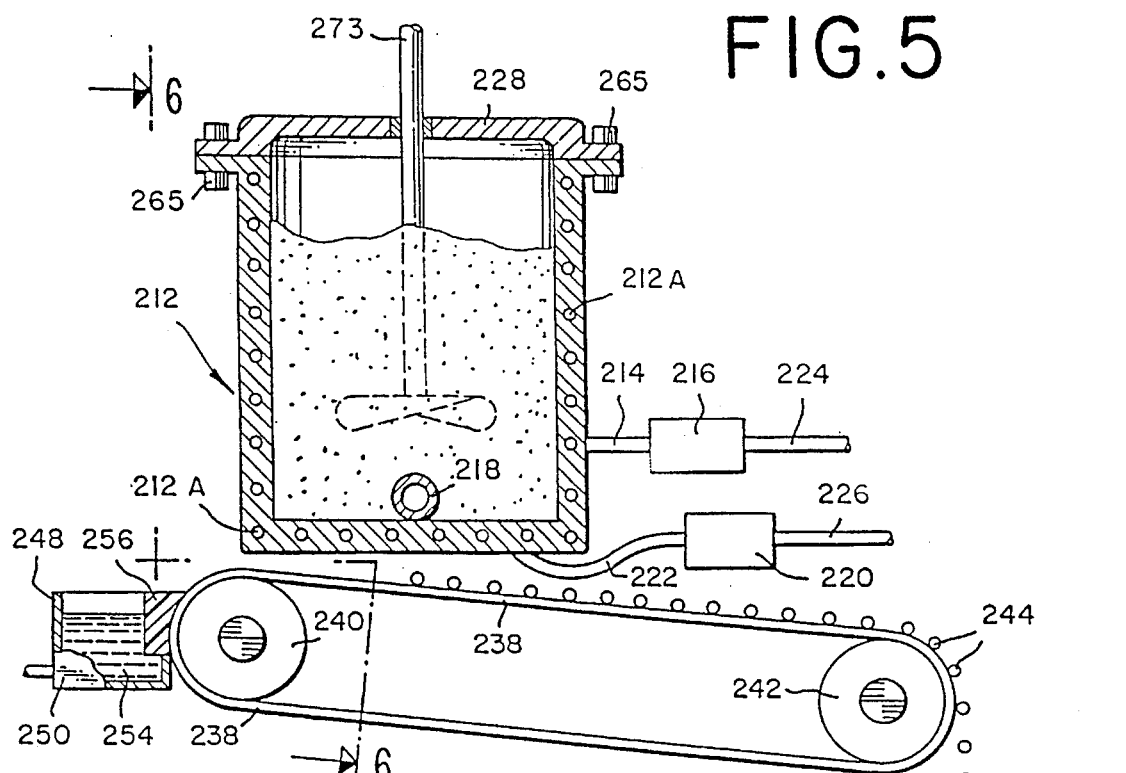

FIG. 5 represents a cut-away side elevation view of apparatus used in forming perfumed polymers which contain embedded therein certain 1-oxo-substituted and unsubstituted isobutyl-4-ethoxy-benzenes and mixtures thereof with bicyclopentadiene derivatives of our invention including the compound having the structure:

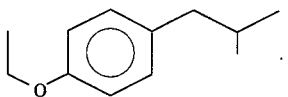

Figure 6:
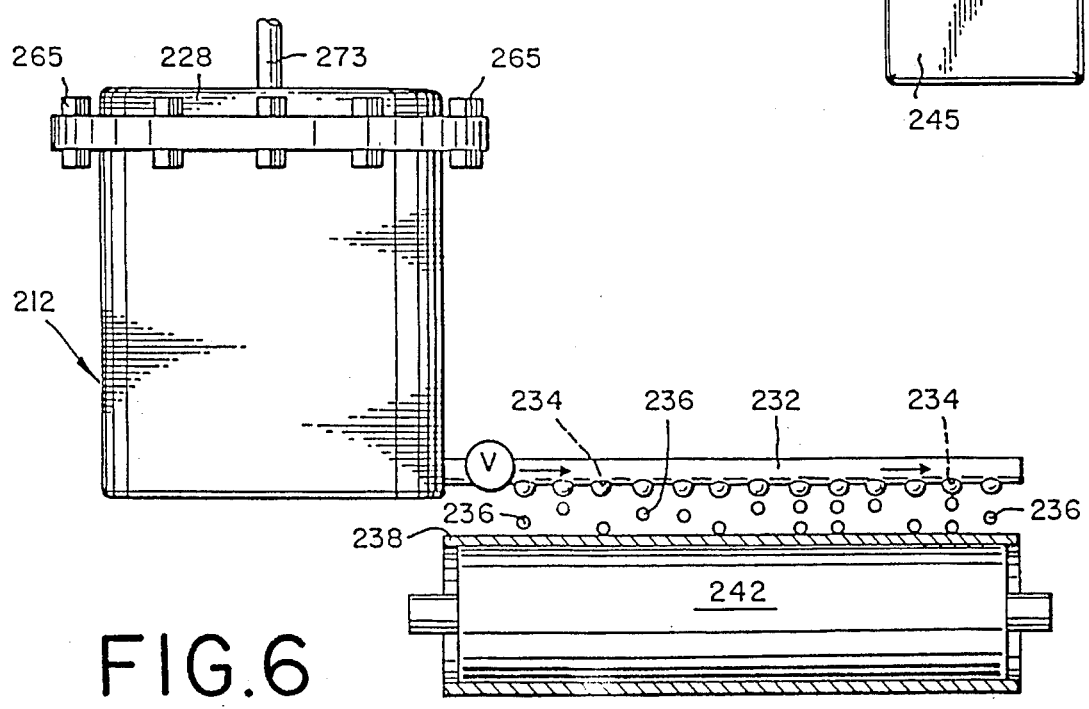

FIG. 6 is a front view of the apparatus of FIG. 5 looking in the direction of the arrows.

DETAILED DESCRIPTION OF THE DRAWINGS

FIG. 1A is the GLC profile for the crude reaction produce of Example I containing the compound having the structure:

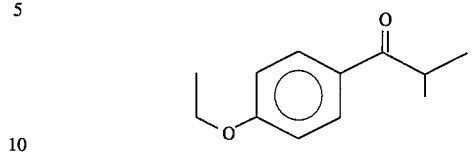

(Conditions: SE-30 column programmed from 80° to 220° C. at 8° C. per minute) The peak indicated by reference numeral 10 is the peak for the compound having the structure:

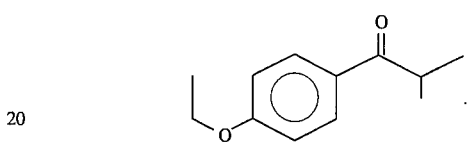

The peak indicated by reference numeral 11 is the peak for the solvent for the reaction, 2-nitropropane having the structure:

FIG. 1B is the GLC profile for the distilled reaction product of Example I. The peak indicated by reference numeral 12 is the peak for the product having the structure:

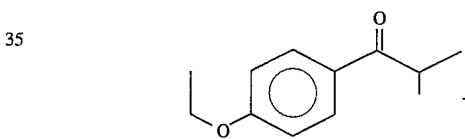

FIG. 3 is the GLC profile for the crude reaction product of Example II The peak indicated by reference numeral 30 is the peak for the compound having the structure:

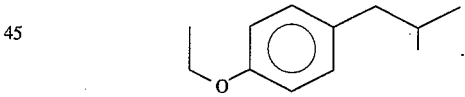

Referring to FIGS. 5 and 6, there is provided a process for forming scented polymer elements (wherein the polymer may be a thermoplastic polymer such as a low density polyethylene or polypropylene or copolymers of ethylene and vinyl acetate or mixtures of polymers and copolymers such as copolymers of ethylene and vinyl acetate and polyethylene) such as pellets useful in the formation of plastic particles useful in fabricating certain articles which may be perfumed (and, further, which may be exposed to chlorine bleaches). This process comprises heating the polymer or mixture of polymers to the melting point of said polymer of mixture of polymers, e.g., 250° C. in the case of low density polyethylene. The lower most portion of the container is maintained at a slightly lower temperature and the material in the container is taken off at such location for delivery through the conduit. Thus, referring to FIGS. 5 and 6, in particular, the apparatus used in producing such elements comprises a device for forming the polymer containing the perfume, e.g., polyethylene or polyethylenepolyvinyl acetate or mixtures of same or polypropylene, which comprises a vat or container 212 into which the polymer taken alone or in admixture with other copolymers and the perfuming substance which is one of the 1-oxo-substituted and unsubstituted isobutyl-4-ethoxy-benzenes and mixtures thereof with bicyclopentadiene derivatives of our invention and other compatible perfumes is placed. The container is closed by means of an air-tight lid 228 and clamped to the container by bolts 265. A stirrer 273 traverses the lid or cover 228 in an air-tight manner and is rotatable in a suitable manner. A surrounding cylinder 212 having heating coils 212A which are supplied with electric current through cable 214 from a rheostat or control 216 is operated to maintain the temperature inside the container 212 such that the polymer in the container will be maintained in the molten or liquid state. It has been found advantageous to employ polymers at such a temperature that the viscosity will be in the range of 90–100 sayboldt seconds. The heater 212A is operated to maintain the upper portion of the container 212 within a temperature range of, for example, 220° 270° C. in the case of low density polyethylene. The bottom portion of the container 212 is heated by means of heating coils 212A regulated through the control 220 connected thereto through a connecting wire 222 to maintain the lower portion of the container 212 within a temperature range of 220°–270° C.

Thus, the polymer or mixture of polymers added to the container 212 is heated from 10–12 hours, whereafter the perfume composition or perfume material which contains at least one of the 1-oxo-substituted and unsubstituted isobutyl-4 -ethoxy-benzenes and mixtures thereof with bicyclopentadiene derivatives of our invention is quickly added to the melt. Generally, about 10–45 percent by weight of the resulting mixture of the perfumery substance is added to the polymer.

After the perfume material is added to the container 212, the mixture is stirred for a few minutes, for example, 5–15 minutes and maintained within the temperature ranges indicated previously by the heating coil 212A. The controls 216 and 220 are connected through cables 224 and 226 to a suitable supply of electric current for supplying the power for heating purposes.

Thereafter the valve "V" is opened permitting the mass to flow outwardly through conduit 232 (also shown in FIG. 5 by reference numeral 218) having a multiplicity of orifices 234 adjacent to the lower side thereof. The outer end of the conduit 232 is closed so that the liquid polymer in intimate contact with at least one of the 1-oxo-substituted and unsubstituted isobutyl-4-ethoxy-benzenes and mixtures thereof with bicyclopentadiene derivatives of our invention and one or more other substances will continuously drop through the orifices 234 downwardly from the conduit 232. During this time, the temperature of the polymer intimately admixed with the perfumery substance in the container 212 is accurately controlled so that a temperature in a range of from about 240°–250° C. (for example, in the case of low density polyethylene) will exist in the conduit 232. The regulation of the temperature through the controls 216 and 220 is essential in order to insure the temperature balance to provide for the continuous dripping or dropping of molten polymer intimately admixed with the perfume substance which is at least one of the 1-oxo-substituted and unsubstituted isobutyl-4-ethoxy-benzenes and mixtures thereof with bicyclopentadiene derivatives of our invention through the orifices 234 at a rate which will insure the formation of droplets 236 which will fall downwardly onto a moving conveyor belt 238 caused to run between conveyor wheels 240 and 242 beneath the conduit 232.

When the droplets 236 fall onto the conveyor 238, they form pellets 244 which harden almost instantaneously and fall off the end of the conveyor 238 into container 245 which is advantageously filled with water or some other suitable cooling liquid to insure the rapid cooling of each of the pellets 244.

Conveyor belt 238 is precooled using cooling sponge 256 which is soaked with cooling water 254 contained in container 250 having container wall 248. The cooling water from sponge 256 impinges on moving conveyor belt 238 to cool it as the conveyor belt 238 is moved by wheels 240 and 242.

Then the pellets 244 are collected from the container 245 and utilized for the formation of functional products, e.g., garbage bags and the like.

THE INVENTION

The present invention provides 1-oxo-substituted and unsubstituted isobutyl-4-ethoxy-benzenes and mixtures thereof with bicyclopentadiene derivatives as well as uses of a number of such 1-oxo-substituted and unsubstituted isobutyl-4-ethoxybenzenes and mixtures thereof with bicyclopentadiene derivatives in augmenting, enhancing or imparting aroma to or in perfume compositions, perfumed articles, perfumed polymers and colognes.

The 1-oxo-substituted and unsubstituted isobutyl-4-ethoxybenzenes of our invention are defined according to the structure:

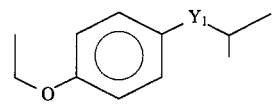

wherein $Y_1$ is a moiety which is in the alternative:

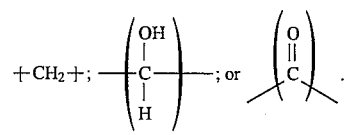

The bicyclopentadiene derivatives useful in the practice of our invention are defined according to the generic structure:

wherein $Z_1$ and $Z_2$ each represents hydrogen, $C_1$–$C_3$ lower alkyl or $C_2$–$C_3$ acyl and wherein $Z_3$ represents hydrogen or methyl with the proviso that $Z_1$ and $Z_2$ are not both hydrogen; and wherein the structure:

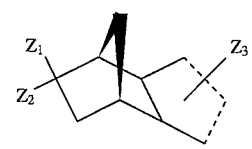

represents a mixture and in the mixture in each of the compounds one of the dashed lines represents a carbon-carbon double bond and the other of the dashed lines represents a carbon-carbon single bond.

The structure:

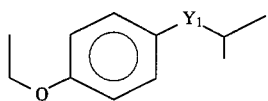

of our invention includes compounds having the structure:

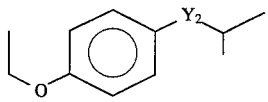

or $Y_2$ represents one of the moieties:

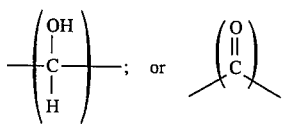

or mixtures of such compounds. The genus of compounds having the structure:

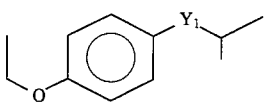

is useful in imparting, augmenting or enhancing aromas in or to perfume compositions, colognes, perfumed articles or perfumed polymers. Furthermore, the mixture of compounds defined according to the structure:

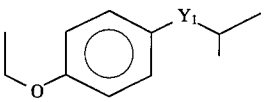

can be taken in combination with compounds having the generic structure:

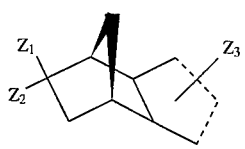

including the compounds having the structures:

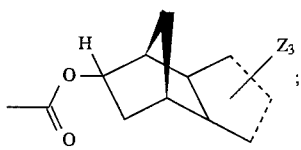

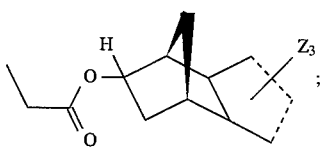

and/or

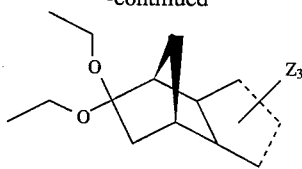

wherein $Z_3$ represents methyl or hydrogen and wherein the dashed lines are as defined, supra.

When the compounds having the structure:

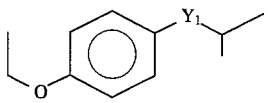

are utilized in admixture with at least one of the compounds having the structure:

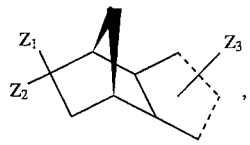

the mole ratio of compounds having the structure:

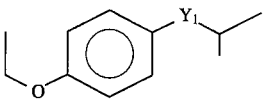

to compounds having the structure:

may vary from about 1:99 down to about 99:1.

The 1-oxo-substituted and unsubstituted isobutyl-4-ethoxybenzenes and mixtures thereof with bicyclopentadiene derivatives of our invention have uses in augmenting or enhancing the aroma of perfume compositions, colognes and perfumed articles including but not limited to perfumed polymers, cosmetic powders, anionic, cationic, nonionic or zwitterionic detergents, fabric softener compositions, fabric softener article including drier added fabric softener articles (e.g., BOUNCE® marketed by the Procter & Gamble Company of Cincinnati, Ohio).

The process of our invention produces a mixture containing a 15 mole percent proportion of the compound having the structure:

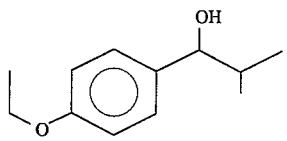

and an 85 mole percent, proportion of the compound having the structure:

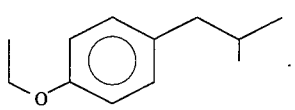

This product can be used "as is" for its perfumery uses or the resulting mixture can be separated into its components and the compound having the structure:

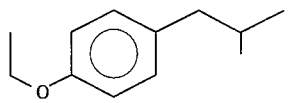

can be used by itself and the compound having the structure:

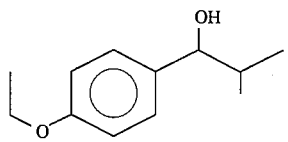

can be used by itself in augmenting, enhancing or imparting perfumery properties to perfumed articles, colognes and/or perfume compositions.

The process of our invention involves first reacting a compound having the structure:

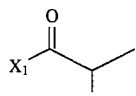

with ethoxybenzene ("Phenetole") having the structure:

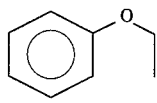

wherein $X_1$ is chloro, bromo or hydroxy according to the reaction:

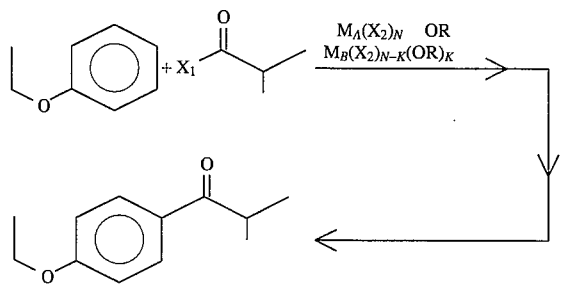

with the reaction taking place in the presence of a Lewis acid catalyst having the structure:

$M_A(X_2)_N$ or having the structure:

$M_B(X_2)_{N-K}(OR)_K$ in the presence of a solvent or in the absence of a solvent. The compound having the structure:

$M_A(X_2)_N$ is a metal halide wherein $M_A$ is a metal such as boron, aluminum, iron, tin or zinc. The halide, $X_2$ is chloro, bromo, iodo or fluoro. N is the valence of the metal $M_A$. Examples of the compound or Lewis acid catalyst having the structure:

$M_A(X_2)_N$ are boron triflouride; aluminum trichloride; ferric chloride; stannic chloride; or zinc chloride. On the other hand, the catalyst useful in the practice of our invention may be a complex such as boron trifluoride etherate, to wit:

$BF_3(C_2H_5OC_2H_5)$

Furthermore, the Lewis acid catalyst useful in the practice of our invention may have the structure:

$M_B(X_2)_{N-K}(OR)_K$ wherein $M_B$ is a metal such as aluminum; wherein $X_2$ is a halide such as chloro; and R represents lower alkyl such as methyl, ethyl or isopropyl. N is the valence of the metal $M_B$ and K represents the number of alkoxy moieties wherein:

$0<K<N$ and wherein:

$N \leq 4$

As stated, supra, the reaction may take place in the presence of or absence of a solvent. Examples of solvents are 2-nitropropane having the structure:

(the most preferred solvent); nitromethane; hydrocarbons; or chlorinated hydrocarbons.

The temperature of reaction may be between about 0° C. up to about 40° C. with a preferred temperature range of from about 0° C. up to about 5° C.

The preferred reactant due to economic reasons is the compound having the structure:

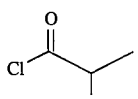

wherein $X_1$ is chloro.

At the end of the reaction, the reaction mass is distilled in order to yield a substantially pure material having the structure:

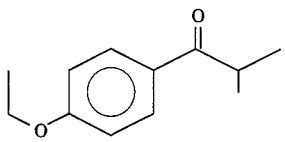

This compound is a novel compound.

The compound having the structure:

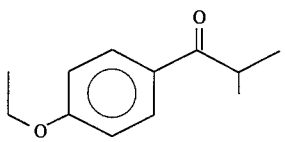

is then used for its organoleptic properties or it may be further reacted by means of reduction using hydrogen and an appropriate hydrogenation catalyst according to the reaction:

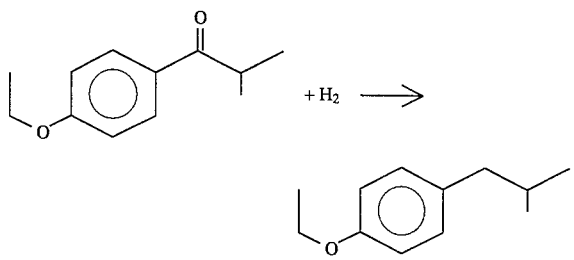

A preferred catalyst is 5% palladium on carbon; although platinum and copper chromite catalysts are also useful. This reaction takes place at a temperature of between about 105° up to about 140° C. in a solvent, preferably isopropyl alcohol and at a pressure in the range of from about 200 psig (pounds per square inch gauge) up to about 500 psig with a preferred reaction pressure of 400 psig. Thus, examples of the preferred reactions of the process of our invention are as follows:

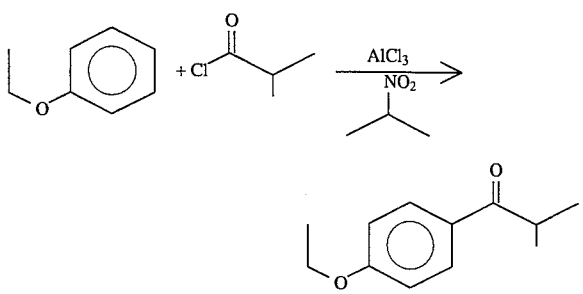

followed by:

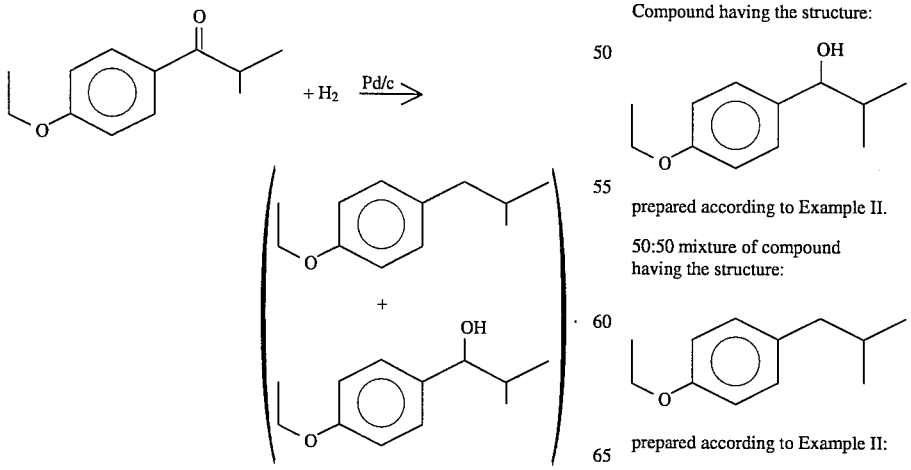

Furthermore, the reaction, to wit:

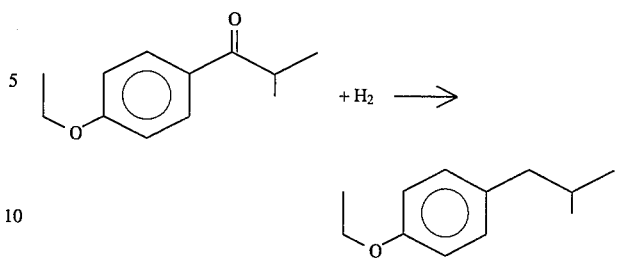

must take place in the presence of a proton source. Examples of a proton source are FILTROL®, an acid ion exchange composition; or phosphoric acid or citric acid.

The following Table I sets forth the perfumery properties of various compositions of matter so useful in perfumery of our invention.

TABLE I

| Description of Composition | Perfumery Properties |
| --- | --- |
| Compound having the structure:<br><br>prepared according to Example II. | A green, woody, privet hedge-like, *(Ligustrum Vulgare)*-like, floral, lilac, ozoney, fennel and anisic aroma with fruity, fresh green, ozoney, fresh air, "ocean breeze", and anisic topnotes. |
| Compound having the structure:<br><br>prepared according to Example II. | A green, woody, privet hedge-like, floral, lilac and ozoney aroma with fruity, fresh green, ozoney, fresh air, and "ocean breeze" topnotes. |
| 85:15 (mole:mole) mixture of compound having the structure:<br><br>: | A green, woody, privet hedge-like, floral, lilac, ozoney, fennel and anisic aroma with fruity, fresh green, ozoney, fresh-air, "ocean breeze" and anisic topnotes. |
| Compound having the structure:<br><br>prepared according to Example II. | |
| 50:50 mixture of compound having the structure:<br><br>prepared according to Example II: | A green, woody, privet hedge-like, floral, lilac, fennel, sweet and anisic aroma with fruity, fresh green, ozoney, fresh-air, "ocean breeze" and anisic topnotes. |

TABLE I-continued

| Description of Composition | Perfumery Properties |
|---|---|
| Compound having the structure: 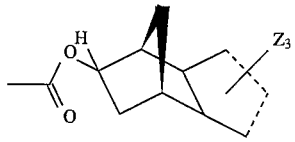 wherein $Z_3$ is hydrogen. | |
| 50:50 (mole:mole) mixture of compound having the structure: 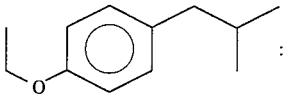 Compound having the structure: 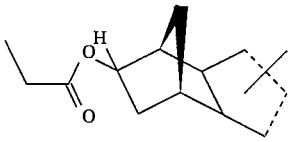 wherein $Z_3$ is hydrogen. | A green, woody, privet hedge-like, floral, lilac, fennel, anisic and basil aroma with fruity, fresh green, ozoney, fresh-air, "ocean breeze" and anisic topnotes. |
| 50:50 (mole:mole) mixture of compound having the structure: 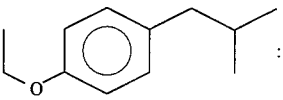 compound having the structure: 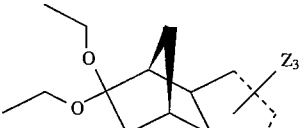 (wherein $Z_3$ is hydrogen). | A fruity basil, hyacinth, green, woody, privet hedge-like, floral, lilac, ozoney, fennel and anisic aroma with fruity, anisic, fresh green, ozoney, fresh-air, and "ocean breeze" topnotes. |
| The compound having the structure: 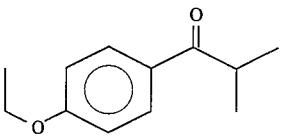 prepared according to Example I. | A green, woody, floral and lilac aroma profile |

The 1-oxo-substituted and unsubstituted isobutyl-4-ethoxybenzenes and mixtures thereof with bicyclopentadiene derivatives of our invention as well as mixtures thereof of our invention and one or more auxiliary perfume ingredients including, for example, hydrocarbons, alcohols (other than the compound having the structure:

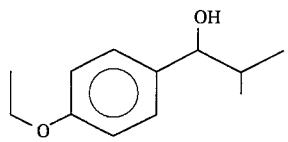

of our invention), ketones (other than the compound having the structure:

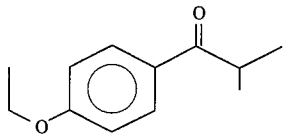

of our invention), aldehydes, nitriles, esters (other than any of the compounds having the structure:

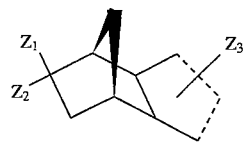

useful in our invention), lactones, ethers (other than the compounds defined according to the genus:

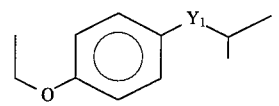

of our invention), hydrocarbons, synthetic essential oils and natural essential oils may be admixed so that the combined odors of the individual components produce a pleasant and desired fragrance particularly and preferably in the "floral/fruity" area. Such perfume compositions usually contain (a) the main note or the "bouquet." or foundation stone of the composition; (b) modifiers which round off and accompany the main note; (c) fixatives which include odorous substances which lend a particular note to the perfume throughout all stages of evaporation and substances which retard evaporation; and (d) topnotes which are usually low boiling, fresh smelling materials.

In perfume compositions it is the individual components which contribute to their particular olfactory characteristics, however, the overall sensory effect of the perfume composition will be at least the sum total of the effects of each of the ingredients. Thus, at least one of the 1-oxo-substituted and unsubstituted isobutyl-4-ethoxy-benzenes and mixtures thereof with bicyclopentadiene derivatives of our invention can be used to alter, modify or enhance the aroma characteristics of a perfume composition, for example, by utilizing or moderating the olfactory reaction contributed by another ingredient in the composition.

The amount of at least one of the 1-oxo-substituted and unsubstituted isobutyl-4-ethoxy-benzenes and mixtures thereof with bicyclopentadiene derivatives of our invention which will be effective in perfume compositions as well as in perfumed articles and colognes depends upon many factors, including the other ingredients, their amounts and the effects which are desired.

It has been found that perfume compositions containing as little as 0.05% of at least one of the 1-oxo-substituted and unsubstituted isobutyl-4-ethoxy-benzenes and mixtures thereof with bicyclopentadiene derivatives of our invention or mixtures thereof can be used to impart, augment or enhance sweet, basil, fruity, hyacinth, fennel, anisic, green, woody, privet hedge-like (*Ligustrum vulgare*)-like, floral, lilac and ozoney aromas with fruity, anisic, fresh green, ozoney, fresh-air, "ocean breeze" topnotes to soaps, cosmetics, detergents (including anionic, cationic, nonionic or zwitterionic solid or liquid detergents) or other products. The amount employed can range up to 70% of the fragrance components and will depend upon considerations of cost, nature of the end product, the effects desired on the finished product and the particular fragrance sought.

At least one of the 1-oxo-substituted and unsubstituted isobutyl-4-ethoxy-benzenes and mixtures thereof with bicyclopentadiene derivatives of our invention are useful (taken alone or together with other ingredients in perfume compositions), in detergents and soaps, space odorants and deodorants, perfumes, colognes, toilet water, bath preparations such as lacquers, brilliantines, pomades and shampoos; cosmetic preparations such as creams, deodorants, hand lotions and sun screens, powders, such as talcs, dusting powders, face powders and the like.

As little as 0.7% of at least one of the 1-oxo-substituted and unsubstituted isobutyl-4-ethoxy-benzenes and mixtures thereof with bicyclopentadiene derivatives of our invention will suffice to impart, augment or enhance a substantive and intense basil, fruity, hyacinth, fennel, anisic, green, woody, privet hedge-like, floral, lilac, and ozoney aromas with fruity, anisic, fresh green, ozoney, fresh-air and "ocean breeze" topnotes to "fruity/floral" perfume formulations.

Generally, no more than 5% of at least one of the 1-oxo-substituted and unsubstituted isobutyl-4-ethoxy-benzenes and mixtures thereof with bicyclopentadiene derivatives of our invention based on the ultimate end product is required to be used "as is" or in the perfume composition.

Furthermore, at least 0.25% of at least one of the 1-oxo-substituted and unsubstituted isobutyl-4-ethoxy-benzenes and mixtures thereof with bicyclopentadiene derivatives of our invention will suffice to impart such aroma to perfumed articles per se, whether in the presence of other perfume materials or whether used by themselves. Thus, the range of use of at least one of the 1-oxo-substituted and unsubstituted isobutyl-4-ethoxy-benzenes and mixtures thereof with bicyclopentadiene derivatives of our invention in the perfumed articles may vary from about 0.25% up to about 5% by weight based on the total weight of the perfumed article In addition, the perfume composition or fragrance composition of our invention can contain a vehicle, or carrier for at least one of the 1-oxo-substituted and unsubstituted isobutyl-4-ethoxy-benzenes and mixtures thereof with bicyclopentadiene derivatives of our invention. The vehicle can be a liquid such as a non-toxic alcohol, e.g., ethanol, a non-toxic glycol, e.g., propylene glycol or the like The carrier can also be an absorbent solid, such as a gum (e.g., gum arabic), or components for encapsulating the composition as by means of coaoervation (such as gelatin).

It will thus be apparent that at least one of the 1-oxo-substituted and unsubstituted isobutyl-4-ethoxy-benzenes and mixtures thereof with bicyclopentadiene derivatives of our invention can be utilized to alter, modify, impart or enhance the aroma of a perfume composition or the aroma to a perfume composition, cologne or perfumed article.

Furthermore, a number of processes known in the art and set forth, for example, in U.S. Pat. No. 5,143,899 issued on Sep. 1, 1992, the specification for which is incorporated by reference herein may be used in order to produce a thickened, highly viscous hypochlorite or hydrogen peroxide bleaching or sterilizing solution, whereby the desired aroma profiles are imparted to the articles treated with such hypochlorite solutions. Specifically, the disclosure as set forth at columns, 12, 13, 14, 15, 16, 17 and 18 of said U.S. Pat. No. 5,143,899 is incorporated by reference herein.

The following Examples I and II serve to illustrate processes for preparing the compounds defined according to the generic structure:

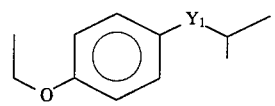

of our invention.

Examples following Example II in general serve to illustrate the organoleptic utilities of the 1-oxo-substituted and unsubstituted isobutyl-4-ethoxy-benzenes and mixtures thereof with bicyclopentadiene derivatives of our invention.

In general, the following examples serve to illustrate specific embodiments of our invention. In will be understood that these examples are illustrative and that the invention is to be considered restricted thereto only as indicated in the appended claims.

All parts and percentages given herein are by weight unless otherwise specified.

EXAMPLE I

PREPARATION OF 1(4'-ETHOXYPHENYL)-2-METHYL PROPANONE-1

Reaction:

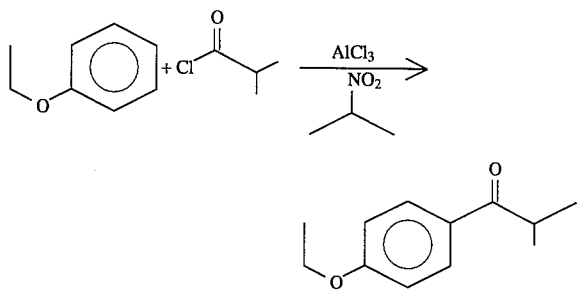

Into a 3 liter reaction vessel equipped with stirrer, thermometer and cooling bath is placed 600 ml of 2-nitropropane having the structure:

With stirring, the 2-nitropropane is cooled to a temperature of between about 0° and about 5° C.

While cooling the vessel using an ice bath 655 grams of aluminum chloride (anhydrous) is added to the reaction mass over a period of one hour.

Over a period of 0.25 hours, with stirring while maintaining the temperature at 0°–5° C., 521 grams of phenetole having the structure:

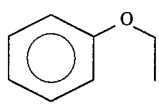

is added to the reaction mass.

Over a period of one hour while maintaining the reaction mass at 0°–10° C., 500 grams of anhydrous isobutyryl chloride having the structure:

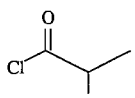

is added to the reaction mass.

With stirring, while maintaining the reaction mass at 0°–5° C. the reaction mass is stirred for a period of two hours.

At the end of the two hour period, the reaction mass is poured onto 1.5 liters of a mixture of ice and water (50:50).

The reaction mass now exists in two phases: an organic phase and an aqueous phase. The organic phase is separated from the aqueous phase. The organic phase is washed with an equal volume of water followed by an equal volume of saturated sodium chloride solution.

The organic phase is then dried over anhydrous magnesium sulfate and filtered.

The resulting reaction mass is then distilled at a vapor temperature of 148° C. liquid temperature 160° C. and vacuum of 8 mm/Hg.

The reaction mass is substantially pure compound having the structure:

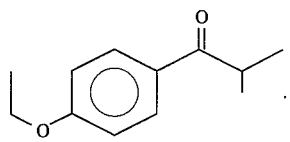

FIG. 1A is the GLC profile of the crude reaction product.
FIG. 1B is the GLC profile of the distilled reaction product.
FIG. 2 is the NMR spectrum for the compound having the structure:

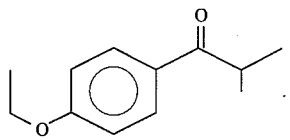

The compound having the structure:

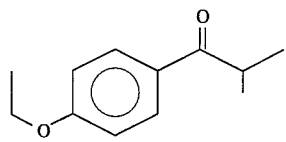

has an intense and substantive green, woody, floral and lilac aroma profile.

EXAMPLE II

PREPARATION OF 1-(4'-ETHOXYPHENYL)-2-METHYLPROPANE AND 1-(4'-ETHOXYPHENYL)-1-HYDROXY-2-METHYLPROPANE

Reaction:

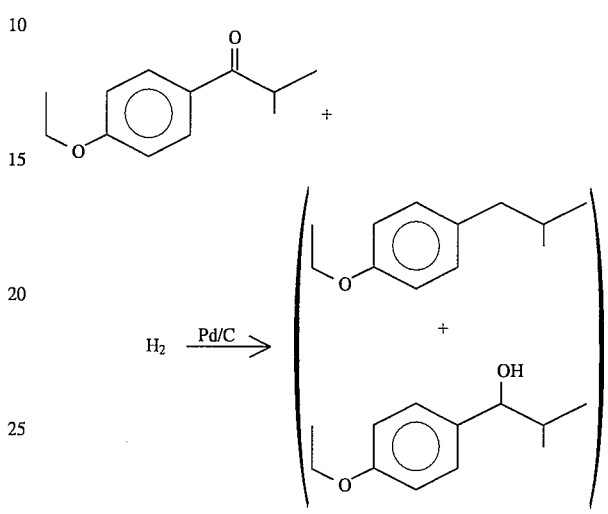

Into a 1 liter autoclave equipped with a hydrogen feed line connected to a compressed hydrogen tank are placed the following ingredients:

360 grams of the compound having the structure:

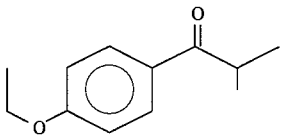

prepared according to Example I;

120 grams anhydrous isopropyl alcohol; and 4.0 grams 5% palladium on carbon supported catalyst.

The autoclave is closed and the hydrogen feeding begins while maintaining the temperature thereof at 105°–115° C. and the pressure inside the autoclave at 400 pounds per square inch gauge (psig). The hydrogen is fed into the autoclave for a period of nine hours while maintaining the autoclave temperature at 105°–130° C. At the end of the nine hour period, the autoclave is cooled and opened and 3 grams of FILTROL® acid ion exchange proton donor is added to the reaction mass. In addition, 3 grams of additional 5% palladium on carbon is added to the reaction mass.

The autoclave is then closed and the hydrogen feed again is commenced at a pressure of 400 psig and at a temperature of 130° C. The hydrogen feed is continued for a period of 2.5 hours.

At the end of the 2.5 hour period, the autoclave is cooled and the contents are removed therefrom and filtered.

The resulting product contains 85% compound having the structure:

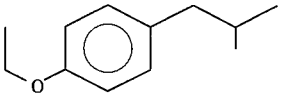

and 15% compound having the structure:

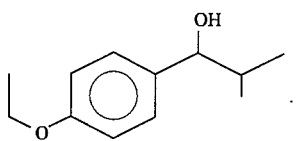

The resulting product is fractionally distilled yielding the following fractions:

| Fraction No. | Vapor Temp. (°C.) | Liquid Temp. (°C.) | Vacuum mm/Hg. Pressure | Reflux Ratio |
|---|---|---|---|---|
| 1 | 23/78 | 73/109 | 50/4 | 4:1 |
| 2 | 82 | 105 | 3.5 | 4:1 |
| 3 | 82 | 106 | 3.5 | 4:1 |
| 4 | 82 | 105 | 3.9 | 4:1 |
| 5 | 82 | 107 | 3.5 | 4:1 |
| 6 | 81 | 108 | 3.5 | 4:1 |
| 7 | 82 | 109 | 3.5 | 1:1 |
| 8 | 82 | 111 | 3.9 | 1:1 |
| 9 | 82 | 116 | 3.5 | 1:1 |
| 10 | 82 | 121 | 3.5 | 1:1 |
| 11 | 80 | 125 | 3.0 | 1:1 |
| 12 | 88 | 133 | 2.5 | 1:1 |
| 13 | 93 | 135 | 1 | 4:1 |
| 14 | 89 | 160 | 1 | 1:1 |
| 15 | 71 | 190 | 1 | 1:1. |

Fractions 5–11 are bulked and redistilled on a new column yielding the following fractions:

| Fraction No. | Vapor Temp. (°C.) | Liquid Temp. (°C.) | Vacuum mm/Hg. Pressure | Reflux Ratio |
|---|---|---|---|---|
| 1 | 23/103 | 23/105 | 20/5 | 9:1 |
| 2 | 102 | 104 | 5 | 9:1 |
| 3 | 103 | 105 | 5 | 9:1 |
| 4 | 101 | 107 | 5 | 1:1 |
| 5 | 102 | 105 | 5 | 1:1 |
| 6 | 102 | 100 | 5 | 1:1 |
| 7 | 102 | 109 | 5 | 1:1 |
| 8 | 96 | 115 | 2 | 1:1. |

Fraction 8 is substantially pure compound having the structure:

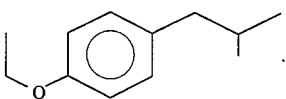

Fractions 2 and 3 are substantially pure compound having the structure:

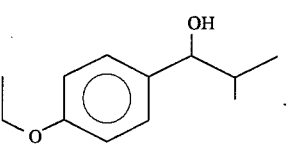

The compound having the structure:

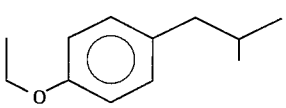

has a green, woody, privet hedge-like, floral, lilac, ozoney, fennel and anisic aroma with fruity, anisic, fresh green, ozoney, fresh-air and "ocean breeze" topnotes. The compound having the structure:

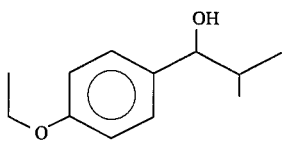

has a green, woody, privet hedge-like, floral, lilac and ozoney aroma with fruity, fresh green, ozoney, fresh-air and "ocean breeze" topnotes.

FIG. 3 is the GLC profile for the crude reaction product of this example. The peak indicated by reference numeral 30 is the peak for the compound having the structure:

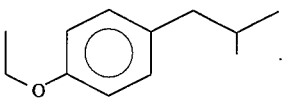

FIG. 4 is the NMR spectrum for the compound having the structure:

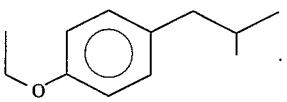

EXAMPLE III

The following Chypre formulations are prepared:

| Ingredients | Parts by Weight | | |
|---|---|---|---|
| | III (A) | III (B) | III (C) |
| Musk ambrette | 40 | 40 | 40 |
| Musk ketone | 60 | 60 | 60 |
| Coumarin | 30 | 30 | 30 |
| Oil of bergamot | 150 | 150 | 150 |
| Oil of lemon | 100 | 100 | 100 |
| Methyl ionone | 50 | 50 | 50 |
| Hexyl cinnamic aldehyde | 100 | 100 | 100 |
| Hydroxycitronellal | 100 | 100 | 100 |
| Oil of lavender | 50 | 50 | 50 |
| Texas cedarwood oil | 15 | 15 | 15 |
| Virginia cedarwood oil | 15 | 15 | 15 |
| Oil of Sandalwood (East Indies) | 20 | 20 | 20 |
| Eugenol | 10 | 10 | 10 |
| Benzyl acetate | 30 | 30 | 30 |
| Alpha-Phenyl ethyl alcohol | 80 | 80 | 80 |
| Beta-Phenyl ethyl alcohol | 90 | 90 | 90 |
| Oakmoss absolute | 30 | 30 | 30 |
| Vetiver oil Venezuela | 10 | 10 | 10 |
| The compound having the structure: 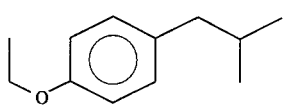 | 80 | 0 | 80 |
| The compound having the structure: | 0 | 80 | 20 |

-continued

| Ingredients | Parts by Weight | | |
|---|---|---|---|
| | III (A) | III (B) | III (C) |
| The compound having the structure: 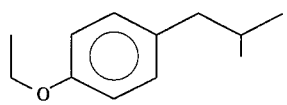 | 0 | 80 | 0 |
| 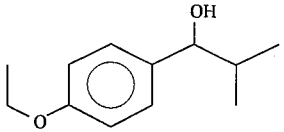 (wherein Z₃ is hydrogen). | | | |

The compound having the structure:

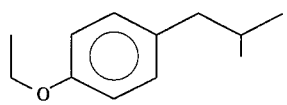

imparts to this Chypre formulation green, woody, privet hedge-like, floral, lilac, ozoney, fennel and anisic undertones with fruity, anisic, fresh green, ozoney, fresh-air and "ocean breeze" topnotes. Accordingly, the perfume formulation of Example III(A) can be described as "a Chypre aroma with fennel, anisic, green, woody, privet hedge-like, floral, lilac and ozoney undertones and fruity, anisic, fresh green, ozoney, fresh-air and "ocean breeze" topnotes".

The mixture of compounds having the structures:

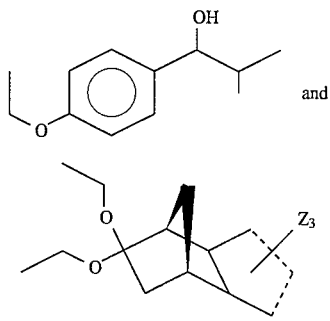

(wherein Z₃ is hydrogen) imparts to this Chypre formulation fruity, basil, hyacinth, green, woody, privet hedge-like, floral, lilac and ozoney undertones with fruity, fresh green, ozoney, fresh-air and "ocean breeze" topnotes. Accordingly, the Chypre formulation of Example III (B) can be described as "a Chypre aroma with fruity, basil, hyacinth, green, woody, privet hedge-like, floral, lilac and ozoney undertones and fruity, fresh green, ozoney, fresh-air and "ocean breeze" topnotes".

The mixture of compounds having the structures:

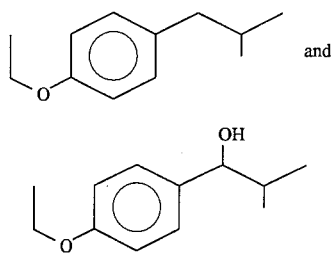

imparts to this Chypre formulation fennel, anisic, green, woody, privet hedge-like, floral, lilac and ozoney undertones with fruity, anisic, fresh green, ozoney, fresh-air and "ocean breeze" topnotes. Accordingly, the Chypre formulation of Example III(C) can be described as "a Chypre aroma with fennel, anisic, green, woody, privet hedge-like, floral, lilac and ozoney undertones and fruity, anisic, fresh green, ozoney, fresh-air and "ocean breeze" topnotes".

EXAMPLE IV

PREPARATION OF COSMETIC POWDER COMPOSITIONS

Cosmetic powder compositions are prepared by mixing in a ball mill 100 grams of talcum powder with 0.25 grams of each of the substances set forth in Table II below. Each of the cosmetic powder compositions has an excellent aroma as described in Table II below:

TABLE II

| Substance | Aroma Description |
|---|---|
| The compound having the structure: 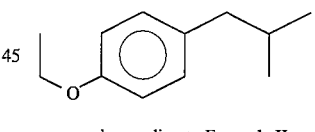 prepared according to Example II. | A fennel, anisic, green, woody, privet hedge-like, floral, lilac and ozoney aroma with fruity, anisic, fresh green, ozoney, fresh-air and "ocean-breeze" topnotes. |
| The compound having the structure: 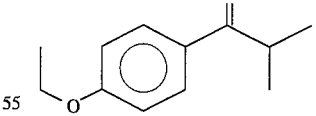 prepared according to Example I. | An intense and substantive green, woody, floral and lilac aroma. |
| The compound having the structure: 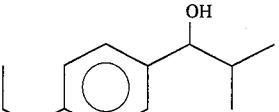 prepared according to Example II. | A green, woody, privet hedge-like, floral, lilac and ozoney aroma with fruity, fresh green, ozoney, fresh-air and "ocean breeze" topnotes. |

TABLE II-continued

| Substance | Aroma Description |
|---|---|
| Mixture of compound having the structure: 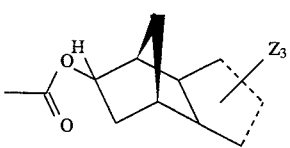 (wherein $Z_3$ is hydrogen) and wherein in the mixture in each of the compounds one of the dashed lines is a carbon-carbon double bond and the other of the dashed lines is a carbon-carbon single bond and the compound having the structure: 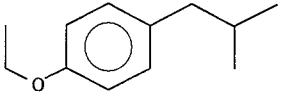 prepared according to Example II. in a 50:50 (mole:mole) admixture. | A sweet, fennel, anisic, green, woody, privet hedge-like, floral, lilac and ozoney aroma with fruity, anisic, fresh green, ozoney, fresh-air and "ocean breeze" topnotes. |
| A 25:75 (mole:mole) mixture of the compound having the structure: 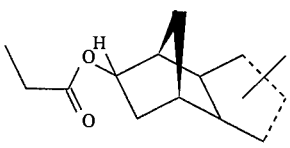 compound having the structure: 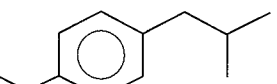 wherein the structure: 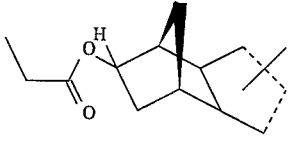 $Z_3$ is hydrogen and in the mixture one of the dashed lines is a carbon-carbon double bond and the other of the dashed lines is a carbon-carbon single bond. | A basil, fennel, anisic, green, woody, privet hedge-like, floral, lilac and ozoney aroma with fruity, anisic, fresh green, ozoney, fresh-air, and "ocean breeze" topnotes. |
| Mixture of compounds (50:50) (mole:mole) having the structure: 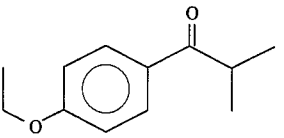 and | A basil, hyacinth, green, woody, floral and lilac aroma profile. |
| 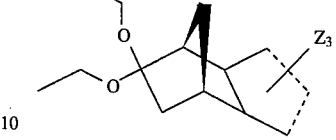 wherein in the composition having the structure: 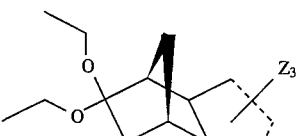 $Z_3$ is hydrogen and in the mixture one of the dashed lines in each of the compounds is a carbon-carbon double bond and the other of the dashed lines is a carbon-carbon single bond. | |
| Perfume composition of Example III(A). | A Chypre aroma with fennel, anisic, green, woody, privet hedge-like, floral, lilac and ozoney undertones and fruity, anisic, fresh green, ozoney, fresh-air and "ocean breeze" topnotes. |
| Perfume composition of Example III(B). | A Chypre aroma with fruity, basil, hyacinth, green, woody, privet hedge-like, floral, lilac and ozoney undertones and fruity, fresh green, ozoney, fresh-air and "ocean breeze" topnotes. |
| Perfume composition of Example III(C). | A Chypre aroma with fennel, anisic, green, woody, privet hedge-like, floral, lilac and ozoney undertones and fruity, anisic, fresh green, ozoney, fresh-air and "ocean breeze" topnotes. |

EXAMPLE V

PERFUMED LIQUID DETERGENT

Concentrated liquid detergents (Lysine salt of n-dodecylbenzene sulfonic acid as more specifically described in U.S. Pat. No. 3,948,818 issued on Apr. 6, 1976) with aroma nuances as set forth in Table II of Example IV are prepared containing 0.10%, 0.15%, 0.20%, 0.25%, 0.30% and 0.35% of the substance set forth in Table II of Example IV. They are prepared by adding and homogeneously mixing the appropriate quantity of substance set forth in Table II of Example IV in the liquid detergent. The detergents all possess excellent aromas as set forth in Table II of Example IV. The intensity increasing with greater concentration of substance set forth in Table II of Example IV.

EXAMPLE VI

PREPARATION OF COLOGNES AND HANDKERCHIEF PERFUMES

Compositions as set forth in Table II of Example IV are incorporated into colognes at concentrations of 2.0%, 2.5%, 3.0%, 3.5%, 4.0%, 4.5% and 5.0% in 80%, 85%, 90% and 95% aqueous food grade ethanol solutions; and into handkerchief perfumes at concentrations of 15%, 20%, 25% and 30% (in 80%, 85%, 90% and 95% aqueous food grade ethanol solutions). Distinctive and definitive fragrances as set forth in Table II of Example IV are imparted to the colognes and to the handkerchief perfumes at all levels indicated.

EXAMPLE VII

PREPARATION OF SOAP COMPOSITIONS

One hundred grams of soap chips [per sample] IVORY®, produced by the Procter & Gamble Company of Cincinnati, Ohio), are each mixed with one gram samples of substances as set forth in Table II of Example IV until homogeneous compositions are obtained. In each of the cases, the homogeneous compositions are heated under 8 atmospheres pressure at 180° C. for a period of three hours and the resulting liquids are placed into soap molds. The resulting soap cakes, on cooling, manifest aromas as set forth in Table II of Example IV.

EXAMPLE VIII

PREPARATION OF SOLID DETERGENT COMPOSITIONS

Detergents are prepared using the following ingredients according to Example I of Canadian Patent No. 1,007,948:

| | |
|---|---|
| "NEODOL ® 45-11 (a $C_{14}$–$C_{15}$ alcohol ethoxylated with 11 moles of ethylene oxide) | 12 |
| Sodium carbonate | 55 |
| Sodium citrate | 20 |
| Sodium sulfate, water brighteners | q.s. |

This detergent is a phosphate-free detergent. Samples of 100 grams each of this detergent are admixed with 0.10, 0.15, 0.20 and 0.25 grams of each of the substances as set forth in Table II of Example IV. Each of the detergent samples has an excellent aroma as indicated in Table II of Example IV.

EXAMPLE IX

Utilizing the procedure of Example I at column 15 of U.S. Pat. No. 3,632,396, non-woven cloth substrates useful as drier-added fabric softening articles of manufacture are prepared wherein the substrate, the substrate coating and the outer coating and the perfuming material are as follows:

1. a water "dissolvable" paper ("Dissolvo Paper");
2. Adogen 448 (m.p. about 140° F.) as the substrate coating; and
3. an outer coating having the following formulation (m.p. about 150° F.):
   57%—$C_{20\text{-}22}$ HAPS;
   22%—isopropyl alcohol;
   20%—antistatic agent;
   1%—of one of the substances as set forth in Table II of Example IV.

Fabric softening compositions prepared according to Example I at column 15 of U.S. Pat. No. 3,632,396 having aroma characteristics as set forth in Table II of Example IV, consist of a substrate coating having a weight of about 3 grams per 100 square inches of substrate; a first coating on the substrate coating consisting of about 1.85 grams per 100 square inches of substrate; and an outer coating coated on the first coating consisting of about 1.4 grams per 100 square inches of substrate. One of the substances of Table II of Example IV is admixed in each case with the outer coating mixture, thereby providing a total aromatized outer coating weight ratio to substrate of about 0.5:1 by weight in the substrate. The aroma characteristics are imparted in a pleasant manner to the head space in a dryer on operation thereof in each case using said drier-added fabric softener nonwoven fabrics and these aroma characteristics are described in Table II of Example IV.

EXAMPLE X

HAIR SPRAY FORMULATIONS

The following hair spray formulation is prepared by first dissolving PVP/VA E-735 a copolymer manufactured by the GAF Corporation of 140 West 51st Street, New York, N.Y., in 91.62 grams of 95% food grade ethanol, 8.0 grams of the polymer is dissolved in the alcohol. The following ingredients are added to the PVP/VA alcoholic solution:

| Ingredients | Weight Percent |
|---|---|
| Dioctyl sebacate | 0.05 |
| Benzyl alcohol | 0.10 |
| Dow Corning 473 fluid (prepared by the Dow Corning Corporation) | 0.10 |
| TWEEN ® 20 surfactant (prepared by ICI America Corporation) | 0.03 |
| One of the perfumery substances as set forth in Table II of Example IV | 0.10 |

The perfuming substances as set forth in Table II of Example IV add aroma characteristics as set forth in Table II of Example IV which are rather intense and aesthetically pleasing to the users of the soft-feel, good hold pump hair sprays.

EXAMPLE XI

CONDITIONING SHAMPOOS

Monamid CMA (prepared by the Mona Industries Company)(3.0 weight percent) is melted with 2.0 weight percent coconut fatty acid (prepared by Procter & Gamble Company of Cincinnati, Ohio); 1.0 weight percent ethylene glycol distearate (prepared by the Armak Corporation) and triethanolamine (a product of Union Carbide Corporation)(1.4 weight percent). The resulting melt is admixed with Stepanol WAT produced by the Stepan Chemical Company (35.0 weight percent). The resulting mixture is heated to 60° C. and mixed until a clear solution is obtained (at 60° C.), GAFQUAT® polymer (manufactured by GAF Corporation of 140 West 51st Street, New York, N.Y.)(5.0 weight percent) is admixed with 0.1 weight percent sodium sulfite and 1.4 weight percent polyethylene glycol 6000 distearate produced by Armak Corporation.

The resulting material is then mixed and cooled to 450° C. and 0.3 weight percent of perfuming substance as set forth in Table II of Example IV is added to the mixture. The resulting mixture is cooled to 40° C. and blending is carried out for an additional one hour in each case. At the end of this blending period, the resulting material has a pleasant fragrance as indicated in Table II of Example IV.

EXAMPLE XII

Four drops of each of the substances set forth in Table II of Example IV, supra, is added separately to two grams of AROMOX® DMC-W to produce a clear premix. The clear premix is added to 200 grams of CLOROX® with stirring resulting in a clear stable, single phase solution. Sufficient 1M aqueous NaOH is added to bring the pH of the mixture up to 12.8. The solution remains substantially stable at 120° F. for a period of seven days. When the aqueous sodium hypochlorite solution is used as a laundry bleach, the resulting laundry, on dry-out in an atmosphere of 65% relative humidity yields substantially no characteristic "hypochlorite" odor, but does have a faint pleasant aroma as set forth in Table II of Example IV. Furthermore, no such characteristic "hypochlorite" aroma is retained on the hands of the individual handling such laundry in both the wet and the dry states.

EXAMPLE XIII

AROMOX® DMMC-W in various quantities is mixed with 0.1 grams of one of the substances set forth in Table II of Example IV, supra. The resulting premixes are then added to 200 grams of an aqueous 5% sodium hypochlorite solution. Sufficient 12.5M aqueous NaOH is added to bring the pH of the mixture up to 13. The following results are obtained:

| Percentage AROMOX ® DMMC-W | Clarity of Hypochlorite solution after addition of premix |
|---|---|
| 0.23% | Clear after three days |
| 0.15% | Clear after three days |
| 0.08% | Initially slightly turbid; two phases exist after three days. |

When the 5% aqueous sodium hypochlorite solution is used as a laundry bleach, the resulting laundry on dry-out, in an atmosphere of 65% relative humidity, yields substantially no characteristic "hypochlorite" odor, but does have a faint, pleasant aroma as set forth in Table II of Example IV. Furthermore, no such characteristic "hypochlorite" aroma is retained on the hands of the individual handling such laundry in both the wet and dry states.

EXAMPLE XIV

Four drops of each of the substances set forth in Table II of Example IV, supra, is added separately to 4 grams of AROMOX® DMC-W to produce a clear premix. The clear premix is added to 200 grams of CLOROX® with stirring resulting in a clear stable single phase solution. Sufficient 1M aqueous LiOH is added to bring the pH of the mixture up to 12.8. The solution remains substantially stable at 120° F. for a period of seven days. When the aqueous lithium hypochlorite solution is used as a laundry bleach the resulting laundry on dry out in an atmosphere of 65% relative humidity yields substantially no characteristic "hypochlorite" odor but does have a faint pleasant aroma as set forth in Table II of Example IV. Furthermore, no such characteristic "hypochlorite" aroma is retained on the hands of the individual handling such laundry in both the wet and the dry states.

What is claimed is:

1. A process for preparing a mixture of compounds having the structures:

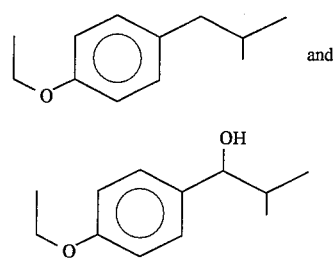

and comprising the steps of first reacting a compound having the structure:

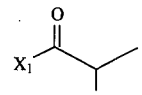

wherein $X_1$ represents chloro, bromo or hydroxy with the compound having the structure:

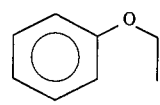

in the presence of a Lewis acid catalyst at a temperature of from 0° up to 40° C. in order to form the substantially pure compound having the structure:

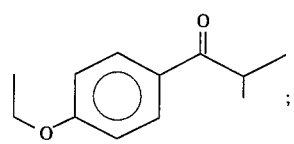

separating the compound having the structure:

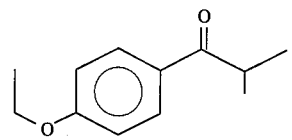

from the reaction mass; and then reacting via a reduction reaction the compound having the structure:

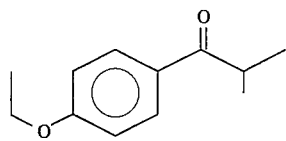

with hydrogen in the presence of a hydrogenation catalyst in an inert solvent at a temperature in the range of from about 105° up to about 140° C. and gauge pressure of from about 200 up to about 500 psig and in the presence of a proton donor whereby a mixture of compounds having the structures:

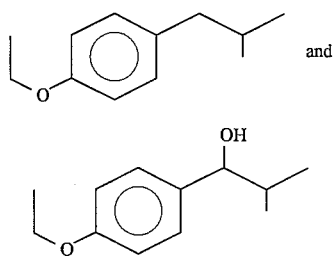

and is formed with 85 mole percent of the reaction product being the compound having the structure:

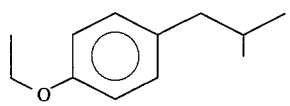

and 15 mole percent of the reaction product being the compound having the structure:

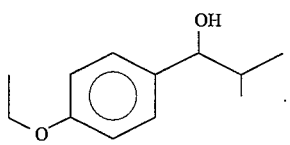

2. The process of claim 1 wherein the reaction sequence is set forth by the reactions:

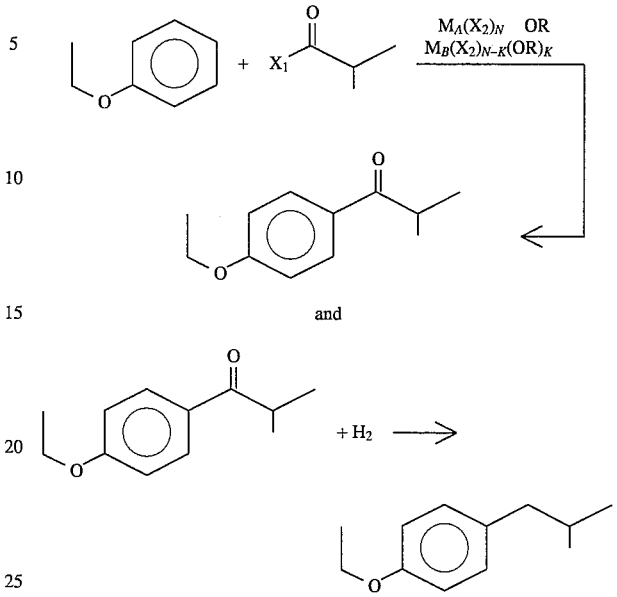

and wherein $M_A$ and $M_B$ represent metals and $X_2$ represents a halide; and R represents lower alkyl and wherein N represents the valence of the metal $M_A$ or $M_B$ and K represents the number of alkoxy moieties with:

$0 < K < N$ and $N \leq 4$.

3. The process of claim 1 wherein the first reaction is carried out in the presence of a 2-nitropropane solvent and the reduction reaction is carried out in the presence of an anhydrous isopropyl alcohol solvent using a 5% palladium on carbon supported catalyst.

* * * * *